United States Patent
Zhang et al.

(10) Patent No.: US 12,127,826 B2
(45) Date of Patent: Oct. 29, 2024

(54) BRAIN ATLAS INDIVIDUALIZATION METHOD AND SYSTEM BASED ON MAGNETIC RESONANCE AND TWIN GRAPH NEURAL NETWORK

(71) Applicant: ZHEJIANG LAB, Hangzhou (CN)

(72) Inventors: Yu Zhang, Hangzhou (CN); Wenyuan Qiu, Hangzhou (CN); Zhichao Wang, Hangzhou (CN); Chaoliang Sun, Hangzhou (CN); Haotian Qian, Hangzhou (CN); Jingsong Li, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 98 days.

(21) Appl. No.: 18/125,640

(22) Filed: Mar. 23, 2023

(65) Prior Publication Data

US 2023/0301542 A1    Sep. 28, 2023

(30) Foreign Application Priority Data

Mar. 24, 2022    (CN) .......................... 202210296098.4

(51) Int. Cl.
*A61B 5/055*    (2006.01)
*G01R 33/48*    (2006.01)
(Continued)

(52) U.S. Cl.
CPC .......... *A61B 5/055* (2013.01); *G01R 33/4806* (2013.01); *G06N 3/042* (2023.01);
(Continued)

(58) Field of Classification Search
CPC ........ A61B 5/055; G01R 33/20; G01R 33/44; G01R 33/48; G01R 33/4806;
(Continued)

(56) References Cited

U.S. PATENT DOCUMENTS

2011/0301431 A1    12/2011    Greicius et al.
2012/0016225 A1    1/2012    Schmidt
(Continued)

FOREIGN PATENT DOCUMENTS

CN    101912263 A    12/2010
CN    103440512 A    12/2013
(Continued)

OTHER PUBLICATIONS

Foo, Heidi, et al. "Age-and sex-related topological organization of human brain functional networks and their relationship to cognition." Frontiers in aging neuroscience 13 (2021): 897.
(Continued)

*Primary Examiner* — Carolyn A Pehlke
(74) *Attorney, Agent, or Firm* — IPro, PLLC

(57) ABSTRACT

The present disclosure discloses a brain atlas individualization method and system based on magnetic resonance and a twin graph neural network. Firstly, a feature is extracted from resting-state functional magnetic resonance imaging (rs-fMRI) by utilizing functional connectivity based on a region-of-interest, and at the same time, Fisher transformation and exponential transformation are performed on the feature; secondly, a corresponding adjacent matrix is extracted from T1-weighted magnetic resonance data in a data set; and then the twin graph neural network is designed for training and testing with the transformed feature and the adjacent matrix as inputs and a group atlas label and a sampling mask as outputs.

8 Claims, 4 Drawing Sheets

(51) Int. Cl.
*G06N 3/042* (2023.01)
*G06T 7/00* (2017.01)

(52) U.S. Cl.
CPC .. *G06T 7/0012* (2013.01); *G06T 2207/10088* (2013.01); *G06T 2207/20084* (2013.01); *G06T 2207/30016* (2013.01)

(58) Field of Classification Search
CPC ....... G16H 30/00–40; G16H 50/00–80; G06N 3/02–10; G06N 20/00; G06T 7/0012
See application file for complete search history.

(56) References Cited

U.S. PATENT DOCUMENTS

| | | |
|---|---|---|
| 2015/0272468 A1 | 10/2015 | Liu et al. |
| 2019/0217112 A1 | 7/2019 | Williams et al. |
| 2020/0225308 A1 | 7/2020 | Dosenbach et al. |
| 2020/0234810 A1 | 7/2020 | Athey et al. |
| 2020/0311926 A1 | 10/2020 | Tian et al. |
| 2021/0169332 A1 | 6/2021 | Zimmerman et al. |
| 2021/0333343 A1 | 10/2021 | Dosenbach |
| 2021/0333344 A1 | 10/2021 | Liang et al. |

FOREIGN PATENT DOCUMENTS

| | | |
|---|---|---|
| CN | 108898135 A | 11/2018 |
| CN | 109496338 A | 3/2019 |
| CN | 109528197 A | 3/2019 |
| CN | 110197729 A | 9/2019 |
| CN | 110298364 A | 10/2019 |
| CN | 110322554 A | 10/2019 |
| CN | 110522448 A | 12/2019 |
| CN | 110811622 A | 2/2020 |
| CN | 111728590 A | 10/2020 |
| CN | 111753947 A | 10/2020 |
| CN | 112002428 A | 11/2020 |
| CN | 112233805 A | 1/2021 |
| CN | 113040715 A | 6/2021 |
| CN | 113539435 A | 10/2021 |
| CN | 113610808 A | 11/2021 |
| CN | 113616184 A | 11/2021 |
| CN | 114376558 A | 4/2022 |
| EP | 3477325 A2 | 5/2019 |
| JP | 2015116213 A | 6/2015 |
| JP | 2019063478 A | 4/2019 |
| JP | 2020028721 A | 2/2020 |
| JP | 2020168372 A | 10/2020 |
| JP | 2021037397 A | 3/2021 |
| JP | 2022503641 A | 1/2022 |
| JP | 2022507861 A | 1/2022 |
| JP | 2023044669 A | 3/2023 |
| WO | 2021223574 A1 | 11/2021 |

OTHER PUBLICATIONS

Cai Wenqin et al. "Advances in Construction of Human Brain Atlases from Magnetic Resonance Images." Chinese Journal of Magnetic Resonance, vol. 37, No. 2. Jun. 9, 2020.

Yi Siwei et al. "Study on the Topological Properties of Whole Brain Dynamic Functional Connectivity Network Based on fMRI Data." Chinese Journal of Applied Probability and Statistics, vol. 34, No. 2. Apr. 15, 2018.

Gao-qi, H. E., et al. "Construction and analysis of brain functionality network based on rs-fMRI data." Journal of East China University of Science and Technology, 6 (2015): 821-827. Dec. 30, 2015.

Wang Kangcheng, et al. "From groupwise to individual brain functional networks parcellation and application." Science China Press, vol. 61, No. 27. Sep. 30, 2016.

Xue, Shao-Wei, et al. "Method for constructing brain functional networks based on fMRI data." Jisuanji Yingyong Yanjiu 27.11 (2010): 4055-4057.

BRAIN ATLAS INDIVIDUALIZATION METHOD AND SYSTEM BASED ON MAGNETIC RESONANCE AND TWIN GRAPH NEURAL NETWORK

The present disclosure claims priority to the Chinese patent application No. 202210296098.4 filed on Mar. 24, 2022 to the China National Intellectual Property Administration and entitled "BRAIN ATLAS INDIVIDUALIZATION METHOD AND SYSTEM BASED ON MAGNETIC RESONANCE AND TWIN GRAPH NEURAL NETWORK", the entire content of which is incorporated herein by reference.

TECHNICAL FIELD

The present disclosure relates to the field of medical imaging and the field of deep learning, in particular to a brain atlas individualization method and system based on magnetic resonance and a twin graph neural network.

BACKGROUND

The cerebral cortex provides an important basis for human perception, movement and other cognitive functions. In the neuroscience, brain regions are of great significance for the cognition, location and analysis of brain functions.

The cerebral cortex region shows different functions, structures, connection relationships and topological structures, so it can be used for brain partitioning by clustering. At present, there are quite a number of non-invasive methods to obtain relevant information in the cerebral cortex, such as magnetic resonance imaging (MRI), magnetoencephalography (MEG), and so on. MRI has become a widely used imaging technology due to its relatively high spatial and temporal resolution, non-radiation and other advantages. Resting-state functional magnetic resonance imaging (rs-fMRI) can reflect the changes of cerebral blood oxygen signals of subjects in a non-task state, and the correlation of these changes can provide sufficient basis for cerebral cortex partitioning, so it is one of the main means to study brain partitioning. Further, resting-state functional connectivity (RSFC) calculated by rs-fMRI can reflect the synchronization of fMRI signals in brain regions, so it can reliably reflect the correlation between cortical apexes. Moreover, RSFC is heritable, is related to gene expression in cortices, and can predict behavioral differences among individuals. Therefore, the construction of many brain atlases is the result of clustering segmentation of brain regions using RSFC signals and averaging among the subjects. This brain atlases based on the average of a large number of subjects, that is, a group atlas (Reference: Schaefer, A., Kong, R., Gordon, E. M., Laumann, T. O., Zuo, X., and Holmes, A. J., et al. (2018). Local-global parcellation of the human cerebral cortex from intrinsic functional connectivity MRI. Cereb. Cortex. 28 (9), 3095-3114.) can provide important observation indicators and statistical data for the macroscopic tissue structure of human brains. However, this brain atlas often lacks the representation of individual differences, especially in regions with significant changes in brain size, spatial position and arrangement. Therefore, if behavioral prediction or disease diagnosis is related to these differences, it is difficult to detect them accurately. Such group atlas has great limitations in the process of constructing biological fingerprint features. Therefore, individualized brain atlases play an increasingly important role in the field of neuroscience and clinical research. The individualized brain atlases can not only predict human cognition, behavior, emotion, etc., but also capture the individual differences in topological structure of the human brains, and can perform gene analysis on these differences. More importantly, the individualized brain atlases can generate biometric fingerprint features of individual brains, which play an important role in prediction and diagnosis of brain degenerative diseases (such as Alzheimer's disease and Parkinson's disease).

Traditional individualized brain atlas algorithms often rely on linear or nonlinear registration of structural imaging in Euclidean space or cortical space. Some machine learning algorithms provide partial analysis tools for these registrations, such as aligning cortical regions through functional regions, anatomical structures, functional connectivity, etc. For example, Wang et al. (Reference: Wang D, Buckner R L, Fox M D, et al. Parcellating cortical functional networks in individuals [J]. Nature neuroscience, 2015, 18(12):1853-1860.) introduce the concept of "core signal", and brain region labels of core signals are updated continuously through functional connectivity and a signal-noise ratio, to reconstruct individualized atlases; Chong et al. (Reference: Chong M, Bhushan C, Joshi A A, et al. Individual parcellation of resting fMRI with a group functional connectivity prior [J]. NeuroImage, 2017, 156:87-100.) iteratively optimize individualized atlases using Bayesian models and sparsity constraint schemes. However, these two methods only use part of the priori knowledge of rs-fMRI signals of the cerebral cortex, and do not explicitly introduce the two pieces of priori knowledge of the consistency of individuals (high similarity of some brain partitions among individuals) and the difference of individuals (large differences of some brain partitions among individuals) into the algorithm. Kong et al. (Reference 1: Kong R, Li J, Orban C, et al. Spatial topography of individual-specific cortical networks predicts human cognition, personality, and emotion [J]. Cerebral cortex, 2019, 29(6):2533-2551. Reference 2: Kong R, Yang Q, Gordon E, et al. Individual-Specific Areal-Level parcellations improve functional connectivity prediction of behavior [J]. bioRxiv, 2021.) reconstruct individualized atlases by establishing a probabilistic graph model and explicitly introducing priori knowledge such as group atlases, inter-subject differences, and intra-subject consistency, which further improves the reconstruction effect of the individualized brain atlases and proves its reasonability. The above schemes still have some disadvantages, such as only considering the characteristics of a single data node or first-order domain node of fMRI, iterative schemes converge slowly and reconstruction time is long.

SUMMARY

For the defects of the prior art, the present disclosure provides a brain atlas individualization method and system based on magnetic resonance and a twin graph neural network. By training on a great amount of subject data and inferring on individualized brain atlases of unknown resting-state magnetic resonance data by utilizing a trained twin graph neural network, reconstruction time can be reduced obviously; and by using a group atlas and a sampling mask as labels, introducing a twin network and adopting a semi-supervised learning manner, the individualized brain atlases can retain high consistency between individuals and reflect the difference between individuals as much as possible. Moreover, since the utilized twin graph neural network adopts a Chebyshev polynomial graph convolutional structure, high-order domain information can be fully utilized, and positioning of brain regions to which apexes belong is more accurate.

The technical solution of the present disclosure is: firstly, functional connectivity and an adjacent matrix are constructed according to rs-fMRI data and T1-weighted MRI data of subjects, the adjacent matrix is converted into an apex-based brain connection graph, and then the functional connectivity is embedded into the brain graph to be used as a network input; then local features between apexes of the brain graph are integrated by using high-order graph convolution, a plurality of convolutional kernels are trained in each graph convolutional layer to encode the difference of cortex regions, moreover, the difference between the subjects is explicitly introduced into a loss function further by utilizing a twin network framework, so as to construct training based on a twin graph convolutional network model; and finally, the concept of high-confidence-coefficient points is introduced, the shortest path length of all the apexes in the group atlas is calculated by utilizing the Floyd-Warshall algorithm, the centrifugal degree of the apexes in each brain region is calculated, a part of points with the small centrifugal degree are taken as points with the high confidence coefficient, and a sampling mask formed by these points is generated, so that, in this way, the consistency between individuals can be further retained, meanwhile, it can be guaranteed that the subjects have enough differences, and the semi-supervised learning mode is designed accordingly.

Specifically, the method includes the following steps:

(1) obtaining magnetic resonance data of subjects, the data being time series data based on apexes of cerebral cortices;

(2) extracting a feature from the magnetic resonance data of the subjects by utilizing functional connectivity RSFC based on a region-of-interest, at the same time, performing Fisher transformation on the extracted feature to normalize the feature, performing exponential transformation on the extracted feature to sparsify the feature, and using the sparsified data as a feature input of the twin graph neural network;

(3) obtaining connection information of surfaces of the cerebral cortices of the subjects according to the magnetic resonance data of the subjects, and calculating an adjacent matrix of each subject as a graph input of the twin graph neural network according to a connection relationship of the apexes of the cerebral cortices described by the connection information;

(4) extracting a central point sampling mask of a group atlas by utilizing a Floyd-Warshall algorithm as a weighting coefficient of a loss function of the twin graph neural network;

(5) adding a difference between the subjects to the network loss function, and training the network by adopting a manner of semi-supervised learning with the central point sampling mask and the group atlas as labels; and (6) giving any magnetic resonance data, inputting the data to the trained twin graph neural network after a feature extracting process same as step (2), mapping one-hot encoding matrices of individualized partitions output by the twin graph neural network at a position of a maximum value as one-dimensional vectors along an encoding dimension to obtain individualized brain atlases corresponding to the magnetic resonance data of the subjects.

Further, the obtained magnetic resonance data of the subjects include rs-fMRI cortex data and T1-weighted magnetic resonance MRI data; and the resting-state functional magnetic resonance imaging rs-fMRI cortex data are used for the functional connectivity RSFC to extract the feature, and the T1-weighted magnetic resonance MRI data are used for calculating the adjacent matrix of the subjects.

Further, during feature extraction through the functional connectivity RSFC, each subject selects the resting-state functional magnetic resonance imaging rs-fMRI data of two scanning sequences from left to right and then selects the group atlas as a reference atlas, the region-of-interest ROI is defined based on the group atlas to calculate an average time series signal of the region, then Pearson correlation is performed on the average time series signal and an average time series signal of the functional magnetic resonance imaging fMRI cortex surface apexes of all the subjects to generate a functional connectivity matrix between the cortex surface apexes and the ROI, each row in the matrix represents a feature vector of the apexes, and then the extracted feature is subjected to data conversion by using Fisher transformation and exponential transformation, wherein formulae of Fisher transformation and exponential transformation are respectively:

$$f = \mathrm{arctanh}(r)$$

$$d = \exp\left(\frac{f}{sig}\right)$$

wherein r is the functional connectivity matrix and is obtained through calculation by using a Pearson correlation coefficient, with a range of $[-1,1]$, f is a result obtained after Fisher transformation, and d is data obtained after exponential transformation, wherein sig controls a scaling range, with a value range of $[0.1, 1]$.

Further, when the adjacent matrix is calculated, the T1-weighted magnetic resonance data are projected to a cerebral cortex with a 32 k resolution so as to obtain corresponding brain atlas connection data, and the adjacent matrix is calculated according to the data to be used as the graph input of the twin graph neural network.

Further, the constructed twin graph neural network includes two graph convolutional network GCN layers with parameters shared, the first layer uses 64 filters, and the number of filters used in the second layer is equal to the number of brain regions of the used group atlas, wherein the filters use Chebyshev convolutional kernels, and the order is 6.

Further, in a process of selecting the group atlas to calculate the sampling mask, for functional magnetic resonance imaging fMRI cortex surface apexes of any given subject, a shortest path distance SPD from a given apex in the adjacent matrix to other fMRI cortex surface apexes is calculated according to the Floyd-Warshall algorithm, and a maximum SPD is taken as a centrifugal degree of the given apex; and for each region-of-interest, the centrifugal degrees are sorted from small to large, first 20% points with the minimum centrifugal degree are selected as points with high confidence coefficients, and the central point sampling mask is extracted.

Further, when the loss function of the twin graph neural network is calculated, data of two subjects and a label of whether the subjects belong to a same subject are provided in each input, and the corresponding loss function includes cross entropy of the group atlas with individualized brain atlases of the two subjects and a contrast loss function between the individualized brain atlases; a weight ratio is 1:1:λ, wherein λ is a hyper-parameter, represented as a weight of the contrast loss function; and a complete loss function of a set of subjects is:

$$L = \sum_i w_i \sum_k y_{i,k} \log(p_{i,k,m}) +$$

$$\sum_i w_i \sum_k y_{i,k} \log(p_{i,k,n}) + \lambda ContrastLoss(p_{i,k,m}, p_{i,k,n}, \text{Label})$$

$$ContrastLoss = (1 + \text{label}) \times \left(\sum_i \sum_k p_{i,k,m} \log(p_{i,k,n})\right)^2 +$$

$$(1 - \text{label}) \times \max\left(\text{threshold} - \left(\sum_i \sum_k p_{i,k,m} \log(p_{i,k,n})\right)^2, 0\right)$$

wherein three items in L represent cross entropy of a probability $y_{i,k}$ that a brain region label of an ith apex is k with brain region predicted values $p_{i,k,m}$, $p_{i,k,n}$ of a subject m and a subject n, and the contrast loss function ContrastLoss respectively; ContrastLoss represents a measurement of a similarity of $p_{i,k,m}$, $p_{i,k,n}$; and $w_1$ is a sampling mask of the ith apex, label=1 represents that a set of input data belongs to the same subject, label=−1 represents that a set of input data belongs to different subjects, and threshold is a threshold value, representing that penalty is only performed when a similarity of the different subjects exceeds the threshold value.

In a second aspect, the present disclosure further provides a brain atlas individualization system based on magnetic resonance and a twin graph neural network, including a data obtaining module, a feature extracting module, an adjacent matrix calculating module, a central point sampling mask extracting module, a twin graph neural network constructing module and an individualized brain atlas module.

The data obtaining module is configured to obtain magnetic resonance data of subjects, the data being time series data based on apexes of cerebral cortices.

The feature extracting module is configured to extract a feature from the magnetic resonance data of the subjects by utilizing functional connectivity RSFC based on a region-of-interest, at the same time, perform Fisher transformation on the extracted feature to normalize the feature, perform exponential transformation on the extracted feature to sparsify the feature, and use the sparsified data as a feature input of the twin graph neural network.

The adjacent matrix calculating module is configured to obtain connection information of surfaces of the cerebral cortices of the subjects according to the magnetic resonance data obtained by the data obtaining module, and calculate an adjacent matrix of each subject as a graph input of the twin graph neural network according to a connection relationship of the apexes of the cerebral cortices described by the connection information.

The central point sampling mask extracting module is configured to extract a central point sampling mask of a group atlas by utilizing a Floyd-Warshall algorithm as a weighting coefficient of a loss function of the twin graph neural network.

The twin graph neural network constructing module is configured to construct the twin graph neural network, add a difference between the subjects to the network loss function, and train the network by adopting a manner of semi-supervised learning with the central point sampling mask and the group atlas as labels.

The individualized brain atlas module is configured to map one-hot encoding matrices of individualized partitions output by the twin graph neural network at a position of a maximum value as one-dimensional vectors along an encoding dimension to obtain individualized brain atlases corresponding to the magnetic resonance data of the subjects.

In a third aspect, the present disclosure further provides a brain atlas individualization apparatus based on magnetic resonance and a twin graph neural network, including a memory and one or more processors, the memory storing executable codes, wherein when the processors execute the executable codes, the brain atlas individualization method based on magnetic resonance and the twin graph neural network is implemented.

In a fourth aspect, the present disclosure further provides a non-transitory computer readable storage medium, storing a program thereon, wherein the program, when executed by a processor, implements the brain atlas individualization method based on magnetic resonance and the twin graph neural network.

The present disclosure has the beneficial effects that by using the group atlas and the central point sampling mask as the labels, the consistency of the individualized atlases and the group atlas is guaranteed, and the individualized atlases are allowed to have high variability at a boundary part; and additionally, by introducing the twin network framework, the consistency of the individualized atlases in the subjects is guaranteed, and meanwhile, the difference of the individualized atlases in different subjects is improved. Meanwhile, compared with other technologies introduced in the background, reconstruction time is greatly shortened while the effectiveness of the individualized atlases is guaranteed. Constructing the reasonable individualized brain atlas for each subject by utilizing the present disclosure is conductive to obtaining more accurate fingerprint feature information of the biology significance, and it has extremely broad applications in the aspects of behavior prediction, genetic analysis, brain disease diagnosis and the like.

DETAILED DESCRIPTION

The detailed description of the present disclosure is further described in detail below in combination with the accompanying drawings.

The present disclosure provides a brain atlas individualization method and system based on magnetic resonance and a twin graph neural network, which show the difference between individuals as far as possible in the case of guaranteeing the consistency of functional regions of subjects. Functional connectivity and an adjacent matrix are constructed according to rs-fMRI data and T1-weighted MRI data of subjects as model inputs; a sampling mask is designed by utilizing a group atlas so as to obtain regions with relatively high consistency as sampling regions, and the group atlas and the sampling mask are introduced into a loss function; a reconstruction model based on the twin graph neural network is designed for training; and finally, in view that there is no true value for assessment of brain atlases, a part of indicators that may assess the reasonability of individualized brain atlases are selected, such as assessing the activation distribution condition of the individualized brain atlases on task-state data. Specific steps are as follows.

Step (1): data obtaining. Magnetic resonance data of HCP 1200S are obtained from the data address of https://db.humanconnectome.org/data/projects/HCP_1200, containing T1-weighted magnetic resonance data, resting-state magnetic resonance data and task-state activation data of 1022 subjects. The magnetic resonance data are obtained by scanning with a 32-channel 3T Siemens magnetic resonance device, wherein TR is 720 ms, and a spatial resolution is 2 mm. All the subjects are scanned within two days respectively to obtain two scanning sequences with phase codes of fMRI from left to right.

Step (2): data preprocessing. The data are processed by using an HCP preprocessing pipeline (https://github.com/Washington-University/HCPpipelines), a specific process is: a) a 4-dimensional time series is generated by utilizing an fMRIVolume pipeline first (e.g., an ".nii.gz" file), wherein this processing includes gradient deconvolution, motion correction, field-pattern-based echo planar imaging EPI distortion correction and the like; b) fMRI data in Euclidean space are mapped to individual cortex data of a 32 k resolution through an fMRIsurface pipeline (e.g., a "dtseries.nii" file), and then a cortex smoothing algorithm based on Gaussian distribution is used for processing; and c) other processing is performed, including: white matter and spinal fluid signals on the obtained cortex data are removed in a regression mode, and a bandwidth filter with a frequency of 0.01 to 0.1 HZ is used for filtering. Relevant descriptions of fMRIVolume, fMRIsurface and other detailed processing methods can be found in the links above.

Figure 1:
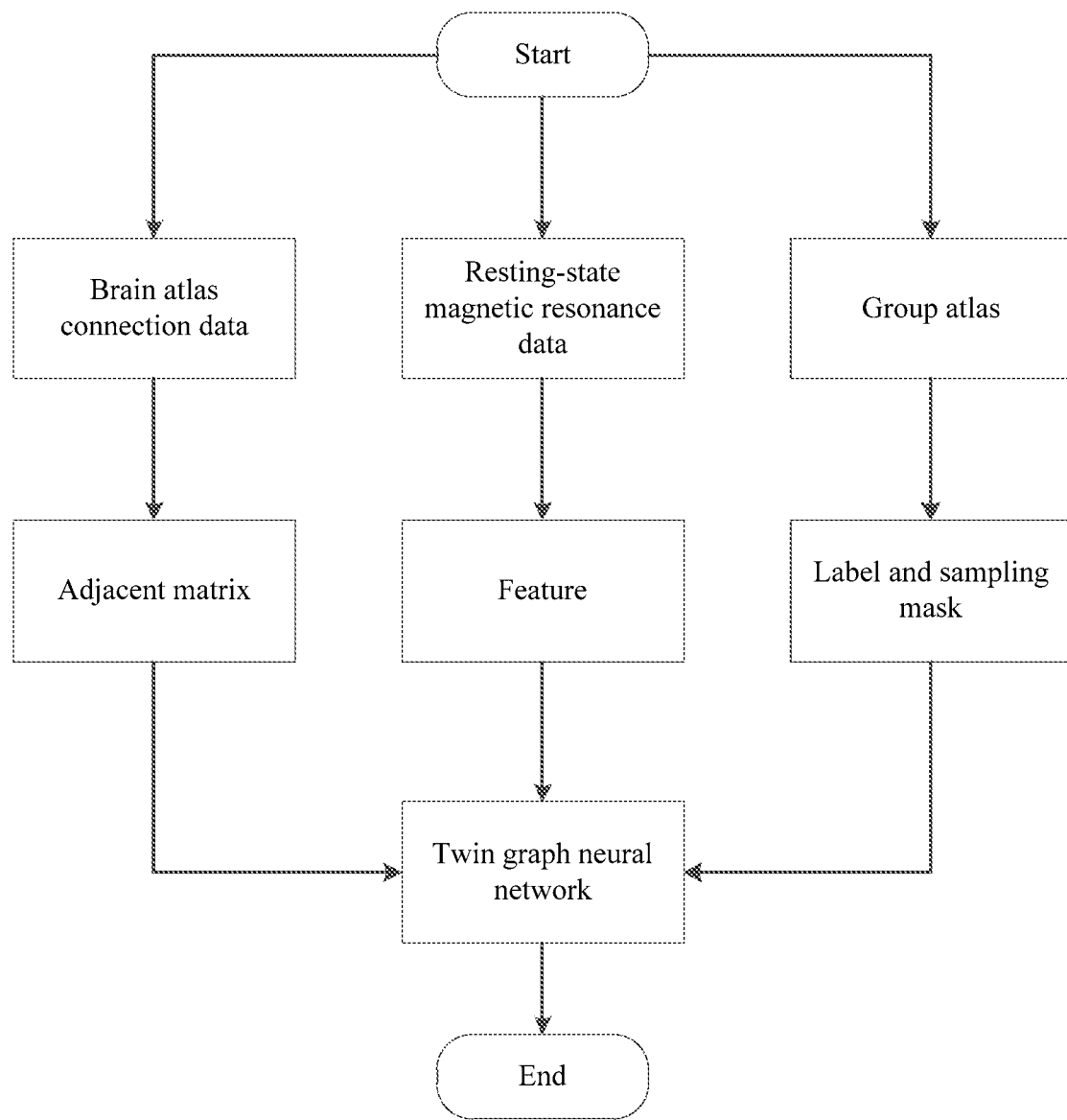
FIG. 1 is a schematic flow diagram of a brain atlas individualization method based on magnetic resonance and a twin graph neural network provided by the present disclosure.

Step (3): construction of feature input X. As shown in FIG. 1, a reference group atlas (Schaefer, A., Kong, R., Gordon, E. M., Laumann, T. O., Zuo, X., and Holmes, A. J., et al. (2018). Local-global parcellation of the human cerebral cortex from intrinsic functional connectivity MRI. Cereb. Cortex. 28 (9), 3095-3114.) and rs-fMRI are selected for feature generation. A region-of-interest (ROI) is defined based on the group atlas, an average value of time series signals of all apexes in each brain region of the group atlas is calculated, and the Pearson correlation of an average time series of the brain regions and a time series of each apex is calculated, so that a functional connectivity matrix between the apexes and the region-of-interest is formed, wherein each row in the matrix represents a feature vector of the apexes, and thus feature dimensionality reduction is achieved, which is used as a feature input X. According to a connection relationship of triangular patches contained in "*.white.32k_fs_LR.surf.gii", an adjacent matrix of the subjects is defined, wherein represents numbers of the subjects.

Step (4): construction of graph input G. Surface layer connection relationship data can be obtained in preprocessing step (2) (*.white.32k_fs_LR.surf.gii), namely "brain atlas connection data" marked in FIG. 1, and by removing points near a brainstem region, apex relationship data of each cortex corresponding to the feature X in step (3) can be obtained. If an apex connection graph is defined for each subject: G=(V, E), then V represents a cortex apex, and E represents the connection relationship between the apexes. By utilizing the gii file, the adjacent matrix of the apexes can be calculated to construct a brain connection graph G. It can be found that the obtained apex connection graph is highly sparse and has prominent local connection characteristics. In most cases, each apex only has connection with 2-6 adjacent apexes around.

Step (5): construction of sampling mask. As shown in FIG. 1, the reference group atlas is selected, a shortest path distance (SPD) from each apex to other apexes in the adjacent matrix is calculated according to a Floyd-Warshall algorithm, and a maximum SPD is taken as a centrifugal degree of the apex. Specifically, taking an apex a in a partition A of the group atlas as an example, a shortest path length from a to other points in A is calculated according to the defined graph G in step (4) by utilizing the Floyd-Warshall algorithm. Then a maximum value of these lengths is used as a centrifugal degree of a in the partition A. Then centrifugal degrees of all points in A are calculated in this way and are sorted in an order of small to large, first 20% points with small centrifugal degrees are selected as a central point set of the region A and are assigned with a label 1, other points are assigned with a label 0, and the points with the value of 1 are defined as points with high confidence coefficients; and centrifugal degree calculation and value assignment are performed on all brain region apexes in a brain in this way, a central point sampling mask can be extracted, and label distribution of the subjects on these points is relatively stable, closer to group atlas labels.

Figure 2:
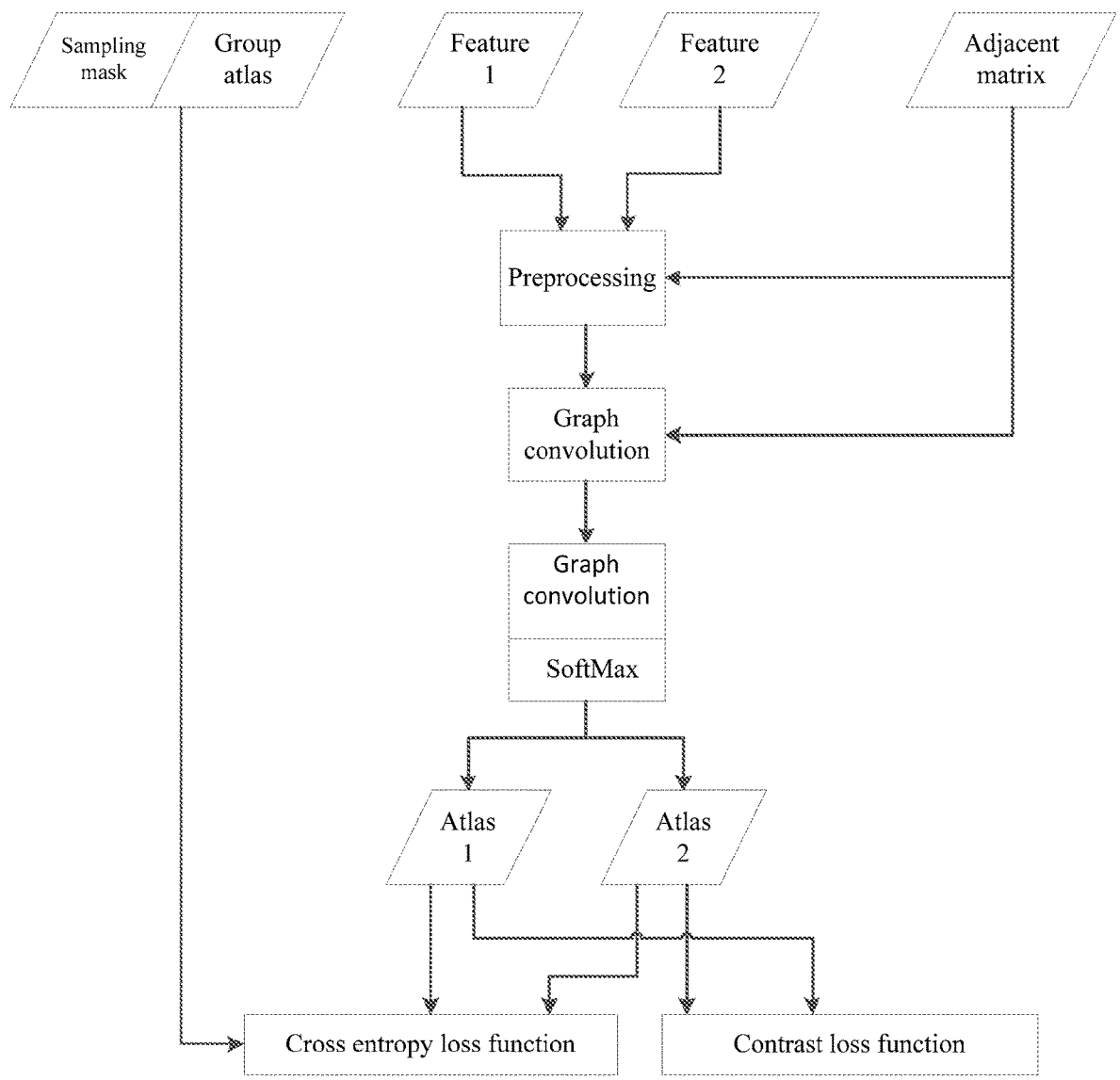
FIG. 2 is a schematic structural diagram of a twin graph neural network of the present disclosure.

Step (6): construction of training set, validation set and testing set. As shown in FIG. 2, 50 subjects are selected, 100 scanning sequences in total, 50 binary data sets are formed randomly, each set containing two scanning sequences, represented by "feature 1" and "feature 2" in FIG. 2, and if the scanning sequences are from the same subject, a label 1 is recorded, otherwise a label −1 is recorded. Then the features in these binary data sets are normalized by using Fisher transformation, and then the features are subjected to exponential transformation and normalization processing to enhance prominent features. The formulae of Fisher transformation and exponential transformation are:

$$f = \operatorname{arctanh}(r)$$

$$d = \exp\left(\frac{f}{sig}\right)$$

wherein r is functional connectivity and is calculated by using a Pearson correlation coefficient, with a range of [−1,1], f is a result obtained after Fisher transformation, and d is data obtained after exponential transformation, wherein sig controls a scaling range, generally with a value range of 0.1 to 1.

Then a training set and a validation set are constructed from the 50 binary sets according to 4:1. 50 subjects are randomly selected from the remaining 972 subjects as a testing set. When the validation set is used, two indicators are selected to be used for selecting the best training model. One of the indicators is a Dice coefficient, which is a set similarity measuring function and is also called a coefficient as an index of similarity. The Dice coefficient is used for predicting an overlapping degree of atlases with the group atlas, and the higher the overlapping degree, the similar individualized atlases to the group atlas. The second indicator is a resting-state consistency coefficient, which is defined to be an average value of every two correlation coefficients of the time series of each partition apex in the individualized atlases, and then averaging is performed once again in all the brain regions. Here, the higher the resting-state consistency coefficient, the more relevant the signals in partitions of the individualized atlases, and the more reasonable the individualized atlases. The best training model is selected by comprehensively considering these two indicators.

Step (7): construction of loss function. The difference between the subjects is added into a network loss function according to the characteristic that the difference between the subjects in the data sets is greater than the difference within the subjects. As shown in FIG. 2, one binary set (i.e., data of two subjects) and a label of whether it belongs to the same subject are input each time to construct cross entropy loss functions of the group atlas with the individualized atlases corresponding to "feature 1" and "feature 2" respectively, and a contrast loss function between the two individualized atlases is added at the same time. The cross entropy loss function represents a gap of distribution of the predicted values of the twin graph neural network and group atlas observation values, and the contrast loss function represents a difference between the two input individualized atlases. A weight ratio is set as 1:1:λ, wherein λ is a hyper-parameter, indicating a weight of the contrast loss function. A complete loss function of a set of subjects is:

$$L = \sum_i w_i \sum_k y_{i,k} \log(p_{i,k,m}) +$$
$$\sum_i w_i \sum_k y_{i,k} \log(p_{i,k,n}) + \lambda ContrastLoss(p_{i,k,m}, p_{i,k,n}, \text{Label})$$
$$ContrastLoss = (1 + \text{label}) \times \left(\sum_i \sum_k p_{i,k,m} \log(p_{i,k,n})\right)^2 +$$
$$(1 - \text{label}) \times \max\left(\text{threshold} - \left(\sum_i \sum_k p_{i,k,m} \log(p_{i,k,n})\right)^2, 0\right)$$

wherein three items in L represent cross entropy of a probability $y_{i,k}$ that a brain region label of the ith apex is k with brain region predicted values $p_{i,k,m}$, $p_{i,k,n}$ of subjects m and n, and the contrast loss function ContrastLoss respectively. ContrastLoss represents a measurement of a similarity of $p_{i,k,m}$, $p_{i,k,n}$. Here, $w_i$ is the sampling mask, label=1 represents that a set of input data belongs to the same subject, label=−1 represents that the set of input data belongs to different subjects, and threshold is a penalty threshold value in the case of different subjects, representing that penalty is only performed when a similarity of the different subjects exceeds this threshold value.

Step (8): construction of twin graph neural network. ChebNet graph convolutional layers based on a Chebyshev polynomial is mainly used in network construction, and graph convolution is specifically defined as follows:

$x *_g g_\theta = \sum_{k=0}^K \theta_k T_k(\tilde{L}) x$   $T_k(x) = 2x T_{k-1}(x) - T_{k-2}(x), T_0(x) = 1, T_1(x) = x$ wherein $*_g$ represents graph convolution, x is graph data (V, E, X), the feature X and the brain connection graph G=(V, E) have been defined in steps (3) and (4), and $g_\theta$ is a convolutional kernel containing a parameter θ and is a network parameter to be trained. k represents an order of adopted ChebNet, with a range of 0 to K, and K is 6 in the present disclosure. $T_k(x)$ represents a Chebyshev polynomial of the kth order.

$$\tilde{L} = \frac{2L}{\eta} - I$$

represents a regularized Laplacian matrix, L is a Laplacian matrix of the graph G, η corresponds to a maximum feature value of the Laplacian matrix, and I is a unit matrix.

A twin network framework is a coupling framework of an artificial neural network, with two samples as an input, representations of the two samples in a new transformation space are output, and the contrast loss function in step (7) is introduced to measure a similarity of the representations of the two samples in the new space. Therefore, binary input sets in a general twin network pass the same neural network and share same network parameters. Specifically, for the present disclosure, the ChebNet graph convolutional layers are added into the network framework respectively, in the first layer of ChebNet, the number of filters is 64, the order is 6, $l_2$ regularization is adopted as a training parameter, and a weight of $l_2$ is 5×10⁻⁴; and in the second layer of ChebNet, the number of filters is determined by the selected reference group atlas, the order is 6, and then a Softmax layer is connected. In order to avoid over-fitting, a dropout layer is connected behind each ChebNet layer, wherein a random drop rate is 0.5. In order to construct the twin graph neural network, the network of this part (two ChebNet layers+two dropout layers+one Softmax layer) is set as parameter sharing, at the same time, a binary set is input, and the network is trained by adopting a manner of semi-supervised learning with the sampling mask and the group atlas as labels. The network is trained by using an Adam optimizer, and a learning rate is 0.01 at the beginning. As for other hyper-parameters, in the loss function, λ=2, threshold=2, in preprocessing, sig=0.1, a training epoch=100, and a training batch_size=2. During training, a model with a minimum corresponding loss function value is reserved, and the twin graph neural network can directly generate individualized brain atlases of other subjects in the testing set.

In order to obtain a whole-brain individualized atlas, the steps above are applied to data sets of the left brain and the right brain respectively. Specifically, cortex data of the "dtseries.nii" file obtained after preprocessing resting-state magnetic resonance by using an HCP preprocessing pipeline contain 59412 apexes in the whole brain, by reading the data header file, the apexes can be split into left brain data of 29696 apexes and right brain data of 29716 apexes, and then reconstruction is completed through the steps above.

Step (9): individualized brain atlases are generated for all the subjects on the testing set by utilizing the twin graph neural network, and assessment is performed on corresponding functional magnetic resonance data. Here, since there is no true value for reference for the individualized brain atlases, assessment can be performed by utilizing "task-state inconsistency". The indicator is defined as an average value of variances of task-state fMRI activation values on all the brain partitions. This average value is averaged again on all the subjects in the testing set to obtain the task-state inconsistency of the testing set. This indicator reflects distribution of activation values of task-state data on the brain partitions. Therefore, a reasonable individualization partition necessarily makes such activation distributed more evenly, that is, the task-state inconsistency is low.

Representative contrast experiments are selected for seven cognitive tasks of HCP respectively, wherein these seven tasks are a motor task, working memory, language processing, emotional processing, social cognition, a gambling task and relational processing respectively. The corresponding representative experiments are as shown in Table 1:

TABLE 1

| Task names | Contrast experiment names |
| --- | --- |
| motor task | right hand movement |
| working memory | 2back conditions on tool images |
| language processing | math vs story |
| emotional processing | faces vs shapes |
| social cognition | theory of mind vs random motion |
| gambling task | reward |
| relational processing | relational processing vs pattern match |

Results show that, compared with the group atlas, in most tasks, the method provided by the present disclosure has obviously lower task-state inconsistency (for example, in a language task, the task inconsistency in the present disclosure is 1.96, while the group atlas is 2.02, and a value $p<0.05$). This indicates that, compared with the group atlas, distribution of task-state fMRI activation of the subjects on the individualized atlases is more uniform, and the reasonability of the individualized atlases reconstructed by using the present disclosure can be demonstrated to a certain extent.

The present disclosure has good expandability. In particular, a group atlas of a 400 partition in the document (Schaefer, A., Kong, R., Gordon, E. M., Laumann, T. O., Zuo, X., and Holmes, A. J., et al. (2018). Local-global parcellation of the human cerebral cortex from intrinsic functional connectivity MRI. Cereb. Cortex. 28(9), 3095-3114.) is mainly used in the present disclosure at present, the target is to generate 400-partition brain atlases of individuals, but the group atlas partition can be replaced, for example, 100, 200 and 1000 are also applicable. Specifically, calculation needs to be performed again according to the defined group atlas when RSFC is obtained in the steps above, central point sampling masks are calculated in the newly-defined group atlas partitions respectively, and network parameters are correspondingly adjusted, for example, the number of the filters in the second graph convolutional layer is adjusted to be a half of the number of the group atlas partitions.

Figure 3:
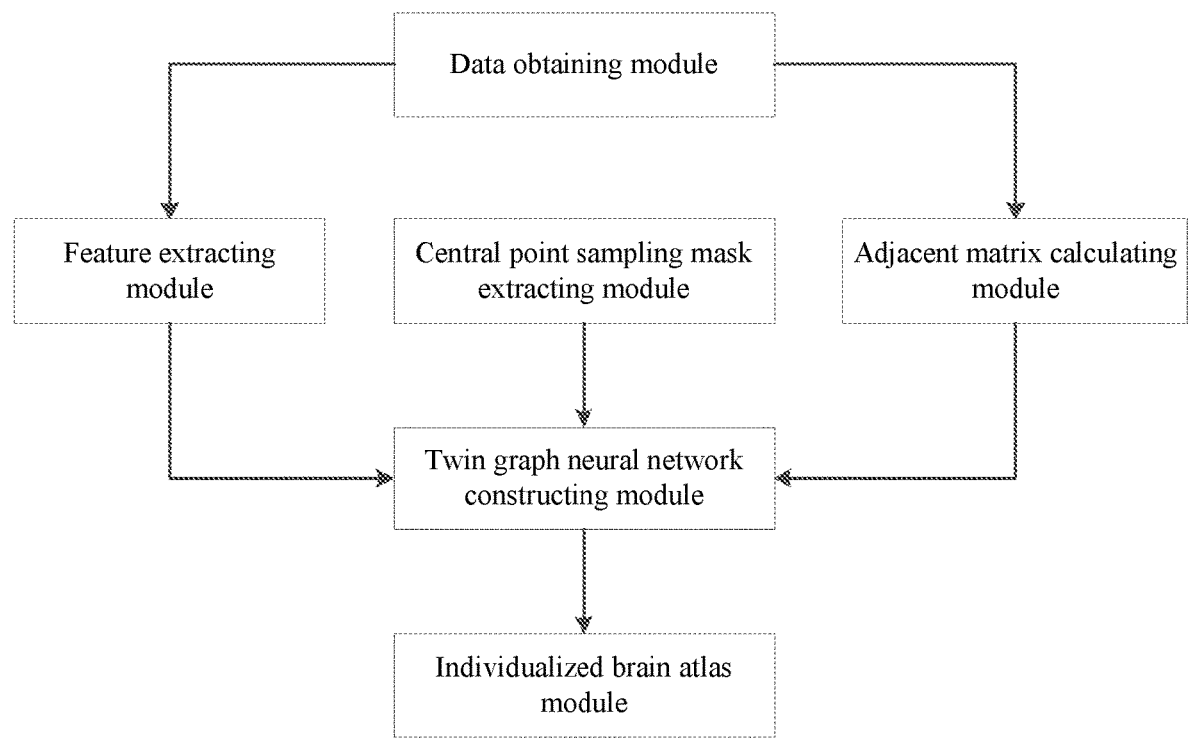
FIG. 3 is a schematic structural diagram of a brain atlas individualization system based on magnetic resonance and a twin graph neural network provided by the present disclosure.

As shown in FIG. 3, in another aspect, the present disclosure further provides a brain atlas individualization system based on magnetic resonance and a twin graph neural network, including a data obtaining module, a feature extracting module, an adjacent matrix calculating module, a central point sampling mask extracting module, a twin graph neural network constructing module and an individualized brain atlas module. Specific function implementing processes of the modules may refer to the corresponding method implementation steps.

The data obtaining module is configured to obtain magnetic resonance data of subjects, the data being time series data based on apexes of cerebral cortices.

The feature extracting module is configured to extract a feature from the magnetic resonance data of the subjects by utilizing functional connectivity RSFC based on a region-of-interest, at the same time, perform Fisher transformation on the extracted feature to normalize the feature, perform exponential transformation on the extracted feature to sparsify the feature, and use the sparsified data as a feature input of the twin graph neural network.

The adjacent matrix calculating module is configured to obtain connection information of surfaces of the cerebral cortices of the subjects according to the magnetic resonance data obtained by the data obtaining module, and calculate an adjacent matrix of each subject as a graph input of the twin graph neural network according to a connection relationship of the apexes of the cerebral cortices described by the connection information.

The central point sampling mask extracting module is configured to extract a central point sampling mask of a group atlas by utilizing a Floyd-Warshall algorithm as a weighting coefficient of a loss function of the twin graph neural network.

The twin graph neural network constructing module is configured to construct the twin graph neural network, add a difference between the subjects to the network loss function, and train the network by adopting a manner of semi-supervised learning with the central point sampling mask and the group atlas as labels.

The individualized brain atlas module is configured to map one-hot encoding matrices of individualized partitions output by the twin graph neural network at a position of a maximum value as one-dimensional vectors along an encoding dimension to obtain individualized brain atlases corresponding to the magnetic resonance data of the subjects.

Corresponding to the embodiment of the brain atlas individualization method based on magnetic resonance and the twin graph neural network, the present disclosure further provides an embodiment of a brain atlas individualization apparatus based on magnetic resonance and a twin graph neural network.

Figure 4:
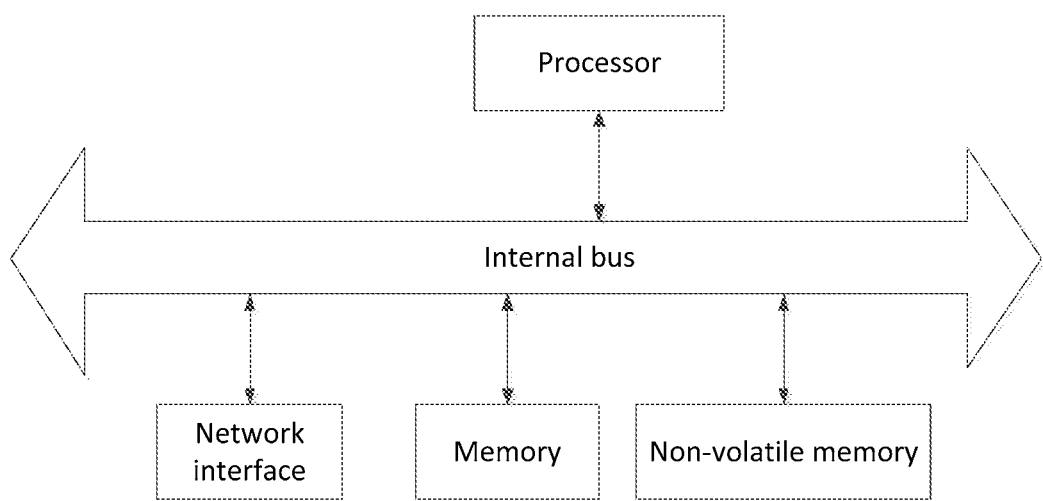
FIG. 4 is a structural diagram of a brain atlas individualization apparatus based on magnetic resonance and a twin graph neural network provided by the present disclosure.

Referring to FIG. 4, the brain atlas individualization apparatus based on magnetic resonance and the twin graph neural network provided by an embodiment of the present disclosure includes a memory and one or more processors, the memory stores executable codes, and when the processors execute the executable codes, the brain atlas individualization method based on magnetic resonance and the twin graph neural network in the above embodiment is implemented.

The embodiment of the brain atlas individualization apparatus based on magnetic resonance and the twin graph neural network of the present disclosure can be applied to any device with data processing capability, and the device with the data processing capability can be a device or apparatus such as a computer. The apparatus embodiment can be implemented by software, hardware or a combination of software and hardware. Taking software implementation as an example, as a logical apparatus, it is formed by reading corresponding computer program instructions in a non-volatile memory into an internal memory through a processor of any device with the data processing capability. In terms of hardware, as shown in FIG. 4, it is a hardware structure diagram of any device with the data processing capability where the brain atlas individualization apparatus based on magnetic resonance and the twin graph neural network of the present disclosure is located. In addition to the processor, internal memory, network interface and non-volatile memory shown in FIG. 4, any device with the data processing capability where the apparatus in the embodiment is located can also include other hardware according to the actual function of any device with the data processing capability, which will not be repeated.

The realization process of the functions and actions of each unit in the above apparatus is detailed in the realization process of the corresponding steps in the above method, and will not be repeated here.

As for the apparatus embodiment, as it basically corresponds to the method embodiment, please refer to the partial description of the method embodiment for related parts. The apparatus embodiment described above is merely illustrative. The units described as separate components may or may not be physically separated, and the components displayed as units may or may not be physical units, that is, they may be located in one place, or it can be distributed to multiple network units. Some or all of the modules can be selected according to actual needs to achieve the purpose of the solution of the present disclosure. Those of ordinary skill in the art can understand and implement it without creative work.

An embodiment of the present disclosure further provides a non-transitory computer readable storage medium, storing a program thereon, wherein the program, when executed by a processor, implements the brain atlas individualization method based on magnetic resonance and the twin graph neural network in the above embodiment.

The non-transitory computer readable storage medium may be an internal storage unit of any device with the data processing capability described in any of the aforementioned embodiments, such as a hard disk or an internal memory. The non-transitory computer readable storage medium may also be an external storage device of any device with the data processing capability, such as a plug-in hard disk, a smart media card (SMC), an SD card, a flash card, etc. provided on the device. Further, the non-transitory computer readable storage medium can also include both the internal storage unit and the external storage device of any device with the data processing capability. The non-transitory computer readable storage medium is used to store the computer program and other programs and data required by any device with the data processing capability, and can also be used to temporarily store data that has been output or will be output.

The above embodiments are used to explain the present disclosure, not to limit the present disclosure, and any modification and change of the present disclosure within the scope of protection of the spirit of the present disclosure and the claims fall within the scope of protection of the present disclosure.

What is claimed is:

1. A brain atlas individualization method based on magnetic resonance and a twin graph neural network, comprising the following steps:

(1) obtaining magnetic resonance data of subjects, the data being time series data based on apexes of cerebral cortices;

(2) extracting a feature from the magnetic resonance data of the subjects by utilizing functional connectivity RSFC based on a region-of-interest, at the same time, performing Fisher transformation on the extracted feature to normalize the feature, performing exponential transformation on the extracted feature to sparsify the feature, and using the sparsified data as a feature input of the twin graph neural network;

(3) obtaining connection information of surfaces of the cerebral cortices of the subjects according to the magnetic resonance data of the subjects, and calculating an adjacent matrix of each subject as a graph input of the twin graph neural network according to a connection relationship of the apexes of the cerebral cortices described by the connection information;

(4) extracting a central point sampling mask of a group atlas by utilizing a Floyd-Warshall algorithm as a weighting coefficient of a loss function of the twin graph neural network; in a process of selecting the group atlas to calculate the sampling mask, for functional magnetic resonance imaging fMRI cortex surface apexes of any given subject, calculating a shortest path distance SPD from a given apex in the adjacent matrix to other fMRI cortex surface apexes according to the Floyd-Warshall algorithm, and taking a maximum SPD as a centrifugal degree of the given apex; and for each region-of-interest, sorting the centrifugal degrees from small to large, selecting first 20% points with the minimum centrifugal degree as points with high confidence coefficients, and extracting the central point sampling mask;

(5) adding a difference between the subjects to the network loss function, and training the network by adopting a manner of semi-supervised learning with the central point sampling mask and the group atlas as labels, wherein when the loss function of the twin graph neural network is calculated, data of two subjects and a label of whether the subjects belong to a same subject are provided in each input, and the corresponding loss function comprises cross entropy of the group atlas with individualized brain atlases of the two subjects and a contrast loss function between the individualized brain atlases; a weight ratio is 1:1:λ, wherein λ is a hyper-parameter, represented as a weight of the contrast loss function; and a complete loss function of a set of subjects is:

$$L = \sum_i w_i \sum_k y_{i,k} \log(p_{i,k,m}) +$$

$$\sum_i w_i \sum_k y_{i,k} \log(p_{i,k,n}) + \lambda ContrastLoss(p_{i,k,m}, p_{i,k,n}, \text{Label})$$

$$ContrastLoss = (1 + \text{label}) \times \left(\sum_i \sum_k p_{i,k,m} \log(p_{i,k,n})\right)^2 +$$

$$(1 - \text{label}) \times \max\left(\text{threshold} - \left(\sum_i \sum_k p_{i,k,m} \log(p_{i,k,n})\right)^2, 0\right)$$

wherein three items in L represent cross entropy of a probability $y_{i,k}$ that a brain region label of an ith apex is k with brain region predicted values $p_{i,k,m}$, $p_{i,k,n}$ of a subject m and a subject n, and the contrast loss function ContrastLoss respectively; ContrastLoss represents a measurement of a similarity of $p_{i,k,m}$, $p_{i,k,n}$; and $w_i$ is a sampling mask of the ith apex, label=1 represents that a set of input data belongs to the same subject, label=−1 represents that a set of input data belongs to different subjects, and threshold is a threshold value, representing that penalty is only performed when a similarity of the different subjects exceeds the threshold value; and (6) giving any magnetic resonance data, and inputting the data to the trained twin graph neural network after a feature extracting process same as step (2), wherein a specific process is: ChebNet graph convolutional layers are added into a network framework, in the first layer of ChebNet, a number of filters of is 64, an order is 6, regularization is adopted as a training parameter, in the second layer of ChebNet, a number of filters is determined by a selected reference group atlas, an order is 6, and then a Softmax layer is connected; in order to avoid over-fitting, a dropout layer is connected behind each ChebNet layer; in order to construct the twin graph neural network, the network of this part is set as parameter sharing, at the same time, a binary set is input, and the network is trained by adopting a manner of semi-supervised learning with the sampling mask and the group atlas as labels; and the network is trained by using an Adam optimizer, during training, a model with a minimum corresponding loss function value is reserved, and one-hot encoding matrices of individualized partitions output by the twin graph neural network are mapped at a position of a maximum value as one-dimensional vectors along an encoding dimension to obtain individualized brain atlases corresponding to the magnetic resonance data of the subjects.

2. The brain atlas individualization method based on magnetic resonance and the twin graph neural network according to claim 1, wherein the obtained magnetic resonance data of the subjects comprise resting-state functional magnetic resonance imaging rs-fMRI cortex data and T1-weighted magnetic resonance MRI data; and the resting-state functional magnetic resonance imaging rs-fMRI cortex data are used for the functional connectivity RSFC to extract the feature, and the T1-weighted magnetic resonance MRI data are used for calculating the adjacent matrix of the subjects.

3. The brain atlas individualization method based on magnetic resonance and the twin graph neural network according to claim 2, wherein during feature extraction through the functional connectivity RSFC, each subject selects the resting-state functional magnetic resonance imaging rs-fMRI data of two scanning sequences with phase codes from left to right and then selects the group atlas as a reference atlas, the region-of-interest ROI is defined based on the group atlas to calculate an average time series signal of the region, then Pearson correlation is performed on the average time series signal and an average time series signal of the functional magnetic resonance imaging fMRI cortex surface apexes of all the subjects to generate a functional connectivity matrix between the cortex surface apexes and the ROI, each row in the matrix represents a feature vector of the apexes, and then the extracted feature is subjected to data conversion by using Fisher transformation and exponential transformation, wherein formulae of Fisher transformation and exponential transformation are respectively:

$$f = \operatorname{arctanh}(r)$$
$$d = \exp\left(\frac{f}{sig}\right)$$

wherein r is the functional connectivity matrix and is obtained through calculation by using a Pearson correlation coefficient, with a range of $[-1,1]$, f is a result obtained after Fisher transformation, and d is data obtained after exponential transformation, wherein sig controls a scaling range, with a value range of $[0.1, 1]$.

4. The brain atlas individualization method based on magnetic resonance and the twin graph neural network according to claim 2, wherein when the adjacent matrix is calculated, the T1-weighted magnetic resonance data are projected to a cerebral cortex with a 32 k resolution so as to obtain corresponding brain atlas connection data, and the adjacent matrix is calculated according to the data to be used as the graph input of the twin graph neural network.

5. The brain atlas individualization method based on magnetic resonance and the twin graph neural network according to claim 1, wherein the constructed twin graph neural network comprises two graph convolutional network GCN layers with parameters shared, wherein the filters use a Chebyshev convolutional kernel.

6. A brain atlas individualization system based on magnetic resonance and a twin graph neural network, comprising a data obtaining module, a feature extracting module, an adjacent matrix calculating module, a central point sampling mask extracting module, a twin graph neural network constructing module and an individualized brain atlas module; wherein the data obtaining module is configured to obtain magnetic resonance data of subjects, the data being time series data based on apexes of cerebral cortices;

the feature extracting module is configured to extract a feature from the magnetic resonance data of the subjects by utilizing functional connectivity RSFC based on a region-of-interest, at the same time, perform Fisher transformation on the extracted feature to normalize the feature, perform exponential transformation on the extracted feature to sparsify the feature, and use the sparsified data as a feature input of the twin graph neural network;

the adjacent matrix calculating module is configured to obtain connection information of surfaces of the cerebral cortices of the subjects according to the magnetic resonance data obtained by the data obtaining module, and calculate an adjacent matrix of each subject as a graph input of the twin graph neural network according to a connection relationship of the apexes of the cerebral cortices described by the connection information;

the central point sampling mask extracting module is configured to extract a central point sampling mask of a group atlas by utilizing a Floyd-Warshall algorithm as a weighting coefficient of a loss function of the twin graph neural network; in a process of selecting the group atlas to calculate the sampling mask, for functional magnetic resonance imaging fMRI cortex surface apexes of any given subject, calculate a shortest path distance SPD from a given apex in the adjacent matrix to other fMRI cortex surface apexes according to the Floyd-Warshall algorithm, and take a maximum SPD as a centrifugal degree of the given apex; and for each region-of-interest, sort the centrifugal degrees from small to large, select first 20% points with the minimum centrifugal degree as points with high confidence coefficients, and extract the central point sampling mask;

the twin graph neural network constructing module is configured to construct the twin graph neural network, add a difference between the subjects to the network loss function, and train the network by adopting a manner of semi-supervised learning with the central point sampling mask and the group atlas as labels, wherein when the loss function of the twin graph neural network is calculated, data of two subjects and a label of whether the subjects belong to a same subject are provided in each input, and the corresponding loss function comprises cross entropy of the group atlas with individualized brain atlases of the two subjects and a contrast loss function between the individualized brain atlases; a weight ratio is $1:1:\lambda$, wherein $\lambda$ is a hyper-parameter, represented as a weight of the contrast loss function; and a complete loss function of a set of subjects is:

$$L = \sum_i w_i \sum_k y_{i,k} \log(p_{i,k,m}) +$$

$$\sum_i w_i \sum_k y_{i,k} \log(p_{i,k,n}) + \lambda ContrastLoss(p_{i,k,m}, p_{i,k,n}, \text{Label})$$

$$ContrastLoss = (1 + \text{label}) \times \left(\sum_i \sum_k p_{i,k,m} \log(p_{i,k,n})\right)^2 +$$

$$(1 - \text{label}) \times \max\left(\text{threshold} - \left(\sum_i \sum_k p_{i,k,m} \log(p_{i,k,n})\right)^2, 0\right)$$

wherein three items in L represent cross entropy of a probability $y_{i,k}$ that a brain region label of an ith apex is k with brain region predicted values $p_{i,k,m}$, $p_{i,k,n}$ of a subject m and a subject n, and the contrast loss function ContrastLoss respectively; ContrastLoss represents a measurement of a similarity of $p_{i,k,m}$, $p_{i,k,n}$; and is a sampling mask of the ith apex, label=1 represents that a set of input data belongs to the same subject, label=−1 represents that a set of input data belongs to different subjects, and threshold is a threshold value, representing that penalty is only performed when a similarity of the different subjects exceeds the threshold value; and the individualized brain atlas module is configured to obtain individualized brain atlases corresponding to the magnetic resonance data of the subjects, wherein a specific process is: ChebNet graph convolutional layers are added into a network framework, in the first layer of ChebNet, a number of filters of is 64, an order is 6, $l_2$ regularization is adopted as a training parameter, in the second layer of ChebNet, a number of filters is determined by a selected reference group atlas, an order is 6, and then a Softmax layer is connected; in order to avoid over-fitting, a dropout layer is connected behind each ChebNet layer; in order to construct the twin graph neural network, the network of this part is set as parameter sharing, at the same time, a binary set is input, and the network is trained by adopting a manner of semi-supervised learning with the sampling mask and the group atlas as labels; and the network is trained by using an Adam optimizer, during training, a model with a minimum corresponding loss function value is reserved, and one-hot encoding matrices of individualized partitions output by the twin graph neural network are mapped at a position of a maximum value as one-dimensional vectors along an encoding dimension to obtain individualized brain atlases corresponding to the magnetic resonance data of the subjects.

7. A brain atlas individualization apparatus based on magnetic resonance and a twin graph neural network, comprising a memory and one or more processors, the memory storing executable codes, wherein when the processors execute the executable codes, the method according to claim 1 is implemented.

8. A non-transitory computer readable storage medium, storing a program thereon, wherein the method according to claim 1 is implemented when the program is executed by a processor.

* * * * *